(12) United States Patent
Medoff et al.

(10) Patent No.: US 8,871,482 B2
(45) Date of Patent: Oct. 28, 2014

(54) BIOPROCESSING

(71) Applicant: Xyleco, Inc., Woburn, MA (US)

(72) Inventors: Marshall Medoff, Brookline, MA (US); Thomas Craig Masterman, Rockport, MA (US); Harrison Medoff, Brookline, MA (US)

(73) Assignee: Xyleco, Inc., Woburn, MA (US)

( * ) Notice: Subject to any disclaimer, the term of this patent is extended or adjusted under 35 U.S.C. 154(b) by 0 days.

(21) Appl. No.: 13/890,717

(22) Filed: May 9, 2013

(65) Prior Publication Data

US 2013/0252305 A1 Sep. 26, 2013

Related U.S. Application Data

(60) Division of application No. 13/293,971, filed on Nov. 10, 2011, now Pat. No. 8,465,956, which is a continuation of application No. PCT/US2010/035302, filed on May 18, 2010.

(60) Provisional application No. 61/252,300, filed on Oct. 16, 2009, provisional application No. 61/180,019, filed on May 20, 2009.

(51) Int. Cl.
| | |
|---|---|
| *C12N 11/14* | (2006.01) |
| *C12P 7/10* | (2006.01) |
| *C12P 7/14* | (2006.01) |
| *C12P 19/02* | (2006.01) |
| *C12P 19/14* | (2006.01) |
| *C12N 11/00* | (2006.01) |
| *C10G 3/00* | (2006.01) |
| *C12P 7/06* | (2006.01) |
| *C12P 1/04* | (2006.01) |

(52) U.S. Cl.
CPC . *C12P 7/10* (2013.01); *C12N 11/14* (2013.01); *C12P 7/06* (2013.01); *C12P 7/065* (2013.01); *C12P 7/14* (2013.01); *C12P 19/02* (2013.01); *C12P 19/14* (2013.01); *C12P 2203/00* (2013.01); *Y02E 50/16* (2013.01); *Y02E 50/17* (2013.01)
USPC ........... 435/176; 208/402; 435/161; 435/170; 435/174

(58) Field of Classification Search
None
See application file for complete search history.

(56) References Cited

U.S. PATENT DOCUMENTS

| | | | | |
|---|---|---|---|---|
| 3,519,538 | A | * | 7/1970 | Messing et al. .............. 435/176 |
| 4,113,566 | A | * | 9/1978 | Hamsher et al. .............. 435/44 |
| 4,816,499 | A | * | 3/1989 | Nomura et al. .............. 523/218 |
| 6,444,437 | B1 | | 9/2002 | Sporleder |
| 7,105,339 | B2 | * | 9/2006 | Hutchens et al. .......... 435/287.9 |
| 7,144,632 | B2 | | 12/2006 | Hayes |
| 7,246,621 | B2 | | 7/2007 | McNeirney |
| 7,527,941 | B1 | | 5/2009 | Hogen et al. |
| 7,931,784 | B2 | | 4/2011 | Medoff |
| 2004/0229984 | A1 | * | 11/2004 | Yamato et al. ............... 524/198 |
| 2006/0040280 | A1 | * | 2/2006 | Lee et al. ......................... 435/6 |

FOREIGN PATENT DOCUMENTS

| | | | |
|---|---|---|---|
| CA | 945921 | A1 * | 4/1974 |
| JP | 62158485 | A | 7/1987 |
| WO | 2003012196 | A2 | 2/2003 |

OTHER PUBLICATIONS

F. Sharmin, S. Rakshit, H. Jayasuriya, "Enzyme Immobilization on Glass Surfaces for the Development of Phosphate Detection Biosensors," Agricultural Engineering International: the CIGR Ejournal. Manuscript FP 06 019, vol. IX. Apr. 2007, pp. 1-12.*
Ernst Hempelmann "Hemozoin Biocrystallization in *Plasmodium falciparum* and the antimalarial activity of crystallization inhibitors" Parasitol Res, Mar. 2007 (published online Nov. 17, 2006), 100(4), pp. 671-676.*
Martinez, M; Hilding-Ohlsson, A; Viale, AA; Gorton, E, "Membrane Entrapped *Saccharomyces cerevisiae* in a Biosensor-Like Device as a Generic Rapid Method to Study Cellular Metabolism" Journal of Biochemical and Biophysical Methods, Apr. 10, 2007, 70(3), pp. 455-464.
Bradshaw OJ, Marsh PO, Hodgson RJ, Visser JM."Effects of Glucose and Fluoride on Competition and Metabolism Within in vitro Dental Bacterial Communities and Biofilms" Caries Res., Mar.-Apr. 2002, 36(2),pp. 81-86 (Abstract only).
Junker, Beth, "Fermentation", Kirk-Othmer Encyclopedia of Chemical Technology, John Wiley & Sons, Inc., published online Jan. 16, 2004, vol. 11, pp. 1-55.
Zheng Chun-ming, Sun Xiao-hong, Yu Ai-min, Wu Guang-jun, Zhang Fu-xiang, Yang Ya-Li, Guan Nai-jia,"Yeast Immobilization of Alginate-based modified HY Zeolite for Fermentation of Fuel Ethanol", Acta Petrolei Sinica (Petroleum Processing Section), Oct. 2008:supplement, Acticle ID:1001-8719(s008)-SUPP-0127-04. English Translation, 7 pages.

* cited by examiner

*Primary Examiner* — Jon P Weber
*Assistant Examiner* — Aaron J Kosar
(74) *Attorney, Agent, or Firm* — Leber Patent Law P.C.

(57) ABSTRACT

Functionalized substrate materials, for example inorganic particles and/or synthetic polymeric particles, are used to enhance bioprocesses such as saccharification and fermentation.

17 Claims, 2 Drawing Sheets

BIOPROCESSING

RELATED APPLICATIONS

This application is a divisional of co-pending application Ser. No. 13/293, 971 filed Nov. 10, 2011, which is a continuation of PCT/US2010/035302, filed May 18, 2010, which claimed priority to U.S. Provisional Application No. 61/180, 019, filed May 20, 2009, and U.S. Provisional Application No. 61/252,300, filed Oct. 16, 2009. The complete disclosure of each of these applications is hereby incorporated by reference herein.

BACKGROUND

Carbohydrates can be converted into other materials by bioprocessing techniques that utilize agents such as microorganisms or enzymes. For example, in fermentation carbohydrates are converted into alcohols or acids by microorganisms, e.g., sugar is converted to alcohol using yeast under anaerobic conditions. When fermentation stops prior to complete conversion of a carbohydrate to a product, e.g., sugar to alcohol, a "stuck" fermentation is said to have occurred.

Other bioprocessing techniques include the enzymatic hydrolysis of cellulosic and lignocellulosic materials into low molecular weight sugars.

SUMMARY

In some instances, the presence of a substrate in a bioprocess facilitates conversion, for example of a low molecular weight sugar to an intermediate or a product or of a cellulosic or lignocellulosic material to a low molecular weight sugar. The inventors have found that including a substrate, e.g., an inorganic or organic material, in a mixture with a low molecular weight sugar, a medium, e.g., a solvent or solvent system, and a microorganism can improve the yield and production rate of an intermediate or a product obtained by conversion of the sugar, for example an alcohol such as ethanol or butanol (e.g., n-butanol). Including the substrate also can prevent incomplete, sluggish, or "stuck" product conversion, e.g., by fermentation. Similarly, the inclusion of a substrate can enhance enzymatic hydrolysis of cellulosic or lignocellulosic materials.

Generally, the invention features methods that include using a microorganism and/or an enzyme that is immobilized on a substrate, e.g., fibers or particles, to convert a carbohydrate to a product.

In one aspect, the invention features a method that includes using a microorganism that is immobilized on a substrate, e.g., inorganic or plastic particles or fibers, to convert a low molecular weight sugar, e.g., sucrose, glucose, xylose, or a mixture of any of these, to an intermediate or a product. In some cases, the substrate is functionalized with functional groups that the substrate does not have in its natural state.

By "immobilized," it is meant that the microorganism or enzyme is bonded, directly or indirectly (e.g., through a chemical linker), to the substrate (e.g., particles or fibers) by covalent, hydrogen, ionic, or equivalent bonding, and/or by mechanical interaction, e.g., between the microorganism and pores of a fiber or particle. Bonding may be created, e.g., by electrically polarizing the substrate material. The interaction can be permanent, semi-permanent, or fleeting. Mechanical interaction may include the microorganism or enzyme nesting in or clinging to pores or other sites of a fiber or particle.

Some implementations include one or more of the following features.

Converting can include allowing the microorganism to convert at least a portion of the low molecular weight sugar to an alcohol, e.g., ethanol or butanol, or to a hydrocarbon or hydrogen. Converting may include fermentation. The microorganism may comprise a yeast, e.g., *S. cerevisiae* and/or *P. stipitis*, or a bacterium, e.g., *Zymomonas mobilis*. The method may further include irradiating the substrate, e.g., inorganic fibers, for example with ionizing radiation, such as a particle beam. The fibers or particles may have a Brunauer Emmett Teller (BET) surface area of greater than 0.25 $m^2/g$, and/or a porosity of at least 70%. In some cases the BET surface area may be greater than 10, 100, 250, 500, or even 1000 $m^2/g$. The method may further include reusing the substrate in a subsequent conversion process.

In another aspect, the invention features a mixture that includes a substrate, e.g., a particulate material, having polar functional groups, a microorganism or enzyme having complementary functional groups, and a liquid medium. In some cases, the substrate comprises fibers, e.g., inorganic fibers or plastic fibers.

In a further aspect, the invention features a composition comprising a substrate, e.g., fibers or particles, having functional groups, and a microorganism or enzyme having complementary functional groups, the microorganism or enzyme being immobilized on the substrate. When fibers are used the fibers may be, for example, inorganic fibers or plastic fibers.

The invention also features a method that includes converting a low molecular weight sugar, or a material that includes a low molecular weight sugar, in a mixture with a substrate, a microorganism, and a solvent or a solvent system, e.g., water or a mixture of water and an organic solvent, to an intermediate or a product. Examples of solvents or solvent systems include water, hexane, hexadecane, glycerol, chloroform, toluene, ethyl acetate, petroleum ether, liquefied petroleum gas (LPG), ionic liquids and mixtures thereof. The solvent or solvent system can be in the form of a single phase or two or more phases. The substrate can be, e.g., in fibrous form. For example, the substrate may comprise inorganic fibers or synthetic fibers, e.g., plastic fibers.

In some instances, having a substrate (e.g., fibers treated by any method described herein or untreated) present during production of an intermediate or a product, such as ethanol, can enhance the production rate of the product. Without wishing to be bound by any particular theory, it is believed that having a solid present, such as a high surface area and/or high porosity solid, can increase reaction rates by increasing the effective concentration of solutes and providing a substrate on which reactions can occur.

For example, an irradiated or an un-irradiated fibrous material, e.g., inorganic materials such as carbon fibers or glass fibers, or synthetic polymeric materials such as plastic fibers, can be added to a fermentation process, such as a corn-ethanol fermentation or a sugarcane extract fermentation, to increase the rate of production by at least 10, 15, 20, 30, 40, 50, 75, or 100 percent, or more, e.g., at least 150 percent or even up to 1000 percent. The fibrous material can have a high surface area, high porosity, and/or low bulk density. In some embodiments, the fibrous material is present in the mixture at a concentration of from about 0.5 percent to about 50 percent by weight, such as between about 1 percent and about 25 percent by weight, or between about 2 percent and about 12.5 percent by weight. In other embodiments, the fibrous material is present in amounts greater than about 0.5 percent by weight, such as greater than about 1, 2, 3, 4, 5, 6, 7, 8, 9, or even greater than about 10 percent by weight. For example, in some embodiments, an oxidized, irradiated, or chemically functionalized fibrous material can be added to a low molecular weight sugar fermentation process, e.g., to enhance fermentation rate and output.

Because the substrate is not itself consumed during the conversion process, the substrate can be reused in multiple batch processes, or can be used continuously for the production of a relatively large volume of the product.

Some implementations include one or more of the following features.

Converting can include allowing the microorganism to convert at least a portion of the low molecular weight sugar to an alcohol, e.g., ethanol or butanol. For example, converting can comprise fermentation. The microorganism can comprise a yeast, e.g., selected from the group consisting of *S. cerevisiae* and *P. stipitis*, or a bacterium such as *Zymomonas mobilis*. The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures may be utilized. Converting can exhibit a % performance of at least 140%, in some cases at least 170%. The equation used to determine % performance for ethanol fermentation is:

% Performance=(ethanol in the sample/ethanol in control)×100

The substrate may comprise a fibrous material. The method can further include irradiating the fibrous material prior to mixing, e.g., with ionizing radiation, for example at a total dosage of at least 5 Mrad. Irradiating can be performed using a particle beam, e.g., an electron beam. In some embodiments, irradiating is performed on the substrate while the substrate is exposed to air, nitrogen, oxygen, helium, or argon. Irradiation can be performed utilizing an ionizing radiation, such as gamma rays, a beam of electrons, or ultraviolet C radiation having a wavelength of from about 100 nm to about 280 nm. Irradiation can be performed using multiple applications of radiation. In some cases, the radiation can be applied at a total dose of between about 10 Mrad and about 150 Mrad, and at a dose rate of about 0.5 to about 10 Mrad/day, or 1 Mrad/s to about 10 Mrad/s. In some embodiments, irradiating includes applying two or more radiation sources, such as gamma rays and a beam of electrons.

In another aspect, the substrate is included in a saccharification process, in which the presence of the substrate can enhance the reaction rate and yield of low molecular weight sugar from a cellulose-containing feedstock. In this aspect, the invention features a method comprising utilizing a saccharifying agent that is immobilized on particles to saccharify a cellulosic or lignocellulosic material. The saccharifying agent can be, for example, an enzyme.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
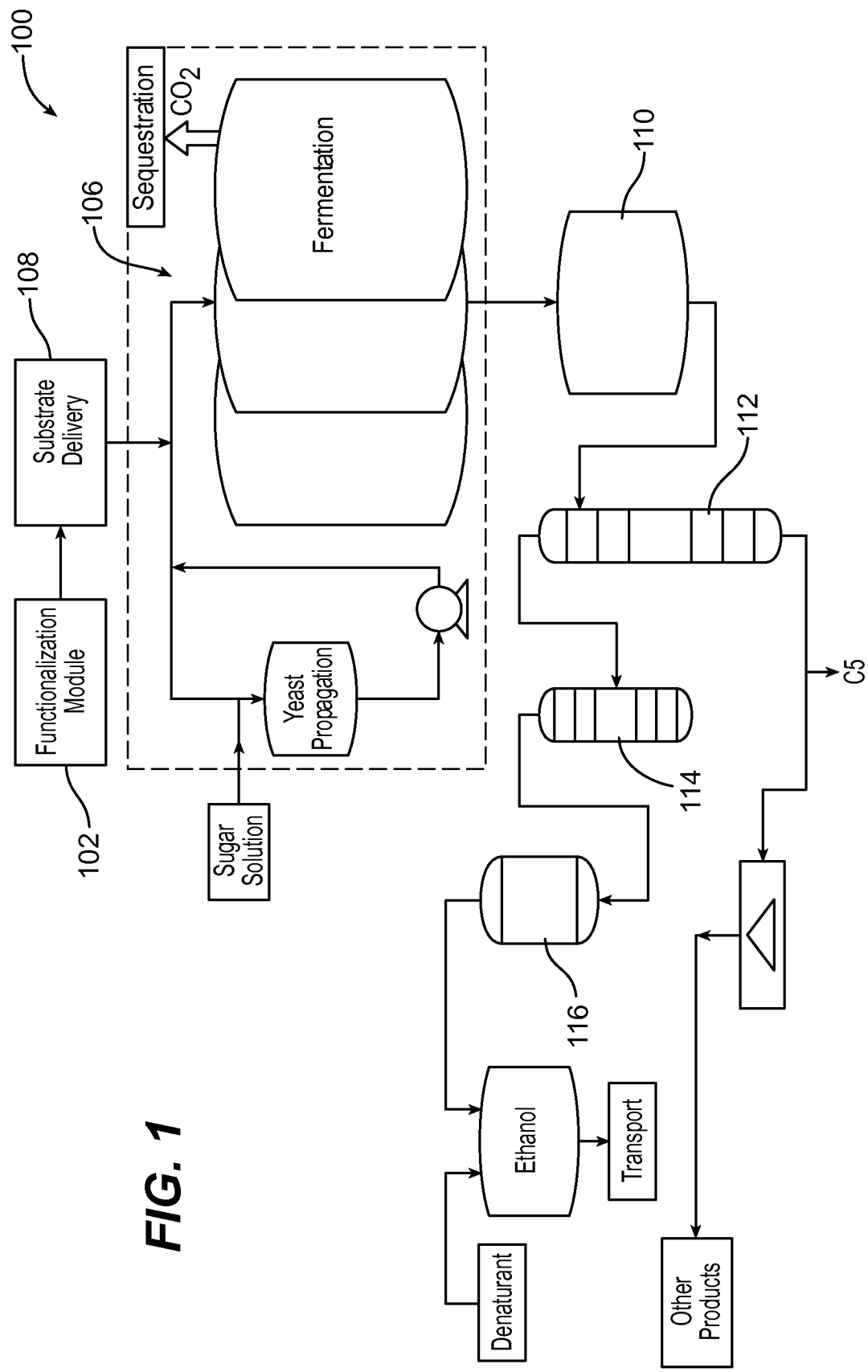
FIG. 1 is a block diagram illustrating treatment of fibers and the use of the treated fibers in a fermentation process.

The substrate materials described herein, e.g., functionalized particulate materials, can facilitate conversion of low molecular weight sugar to an intermediate or a product, e.g., during a fermentation process. Functionalized substrate materials having desired types and amounts of functionality, such as carboxylic acid groups, enol groups, aldehyde groups, ketone groups, nitrile groups, nitro groups, or nitroso groups, can be prepared using the methods described herein or other known methods.

Substrate Materials

The materials discussed below can be functionalized with functional groups that are complementary with functional groups on an agent to be used in converting a low molecular weight sugar, e.g., functional groups present on a microorganism such as yeast.

Suitable substrate materials include organic and inorganic particulate materials. Substrate materials include, for example, inorganic fillers such as calcium carbonate, (e.g., precipitated calcium carbonate or natural calcium carbonate), aragonite clay, orthorhombic clays, calcite clay, rhombohedral clays, kaolin clay, bentonite clay, dicalcium phosphate, tricalcium phosphate, calcium pyrophosphate, insoluble sodium metaphosphate, magnesium orthophosphate, trimagnesium phosphate, hydroxyapatites, synthetic apatites, alumina, hydrated alumina, silica xerogel, metal aluminosilicate complexes, sodium aluminum silicates, zirconium silicate, silicon dioxide graphite, wollastonite, mica, glass, fiber glass, silica, talc, carbon fibers, conductive carbon black, ceramic powders and ceramic fibers, and alumina trihydrate. Other particulate materials can also be used, e.g., ground construction waste, ground tire rubber, lignin, maleated polypropylene, nylon fibers or other thermoplastic fibers, and fluorinated polymers, e.g., fluorinated polyethylene. Combinations of the above materials can also be used.

Some materials are available commercially in a functionalized state. For example, carboxyl-functionalized carbon nanotubes are commercially available, e.g., from NanoLab, Newton, Mass., USA, and functionalized silica gels are commercially available from Isco, Inc.

The particulate materials can have, e.g., a particle size of greater than 1 micron, e.g., greater than 2 microns, 5 microns, 10 microns, 25 microns or even greater than 35 microns. Other physical properties of preferred substrates will be described below.

Nanometer scale fillers can also be used alone, or in combination with fibrous materials of any size and/or shape. The fillers can be in the form of, e.g., a particle, a plate or a fiber. For example, nanometer sized clays, silicon and carbon nanotubes or bucky balls, and silicon and carbon nanowires can be used. The filler can have a transverse dimension less than 1000 nm, e.g., less than 900 nm, 800 nm, 750 nm, 600 nm, 500 nm, 350 nm, 300 nm, 250 nm, 200 nm, less than 100 nm, or even less than 50 nm.

In some embodiments, the nano-clay is a montmorillonite. Such clays are available from Nanocor, Inc. and Southern Clay products, and have been described in U.S. Pat. Nos. 6,849,680 and 6,737,464. The clays can be surface treated before mixing into, e.g., a resin or a fibrous material. For example, the clay can be surface treated so that its surface is ionic in nature, e.g., cationic or anionic.

Aggregated or agglomerated nanometer scale fillers, or nanometer scale fillers that are assembled into supramolecular structures, e.g., self-assembled supramolecular structures, can also be used. The aggregated or supramolecular fillers can be open or closed in structure, and can have a variety of shapes, e.g., cage, tube or spherical.

Blends of any substrate materials described herein can be utilized for making any of the products described herein.

Systems for Functionalizing Substrate Materials and Using Substrate Materials in Fermentation FIG. 1 shows a system 100 for treating a substrate material, e.g., a fibrous or particulate material, and then using the treated material to enhance a fermentation process. System 100 includes an optional module 102 in which the substrate material is functionalized, e.g., by irradiation, oxidation, chemical functionalization, or other means. If the substrate material is to be used in its native state, or has been pre-functionalized, this step is omitted.

The treated substrate material, e.g., functionalized particles or fibers, is delivered to a fermentation system 106 by a substrate delivery module 108. The substrate material may be delivered in any desired concentration, e.g., from about 0.05% to about 20%, about 0.1% to about 10%, about 0.2% to about 6%, or about 0.3% to about 4%. Concentration will be dictated in part by the properties of the substrate material used and how much of the substrate material can be added as a practical matter.

Figure 1A:
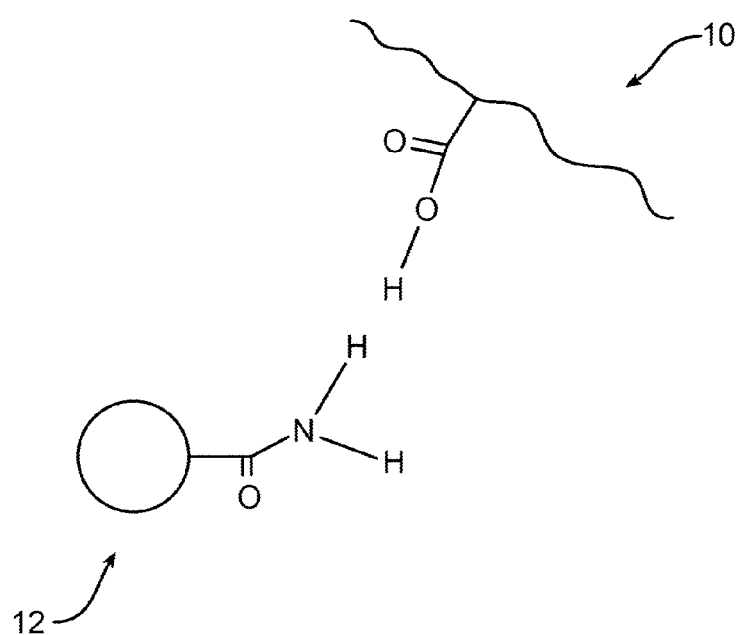
FIG. 1A is a schematic representation of a functionalized fiber interacting with a microorganism.

The functionalized substrate material is then present during fermentation and enhances the fermentation process by providing a substrate that can interact with the microorganisms used in fermentation, e.g., yeast cells. This interaction is shown schematically in FIG. 1A, which depicts a functionalized polar fiber 10 and a yeast cell 12 having a complementary polar functional group. Due to the polarity of the fibers and the yeast cell, the cell can become immobilized on one or more of the fibers. Bonding of the yeast cell (or other microorganism) to the fibers may be by hydrogen bonding, or by covalent or ionic bonding. In some cases, the functional groups on the fibers may react with those on the microorganism, forming a covalent bond. The high surface area and porosity of the fibers provides a large surface area for interaction of the fiber and microorganism and thus enhances this interaction. The immobilized cells are more productive, increasing the efficiency and yield of the fermentation process and preventing the process from becoming prematurely "stuck."

It is noted that if mixing is performed during fermentation, the mixing is preferably relatively gentle (low shear) so as to minimize disruption of the interaction between the microorganisms and fibers. In some embodiments, jet mixing is used, as described in U.S. Provisional Application Nos. 61/179, 995, filed May 20, 2009, and 61/218,832, filed Jun. 19, 2009, and U.S. patent application Ser. No. 12/782,694 filed May 18, 2010 now U.S. Pat. No. 8,636,402. The complete disclosure of each of these applications is incorporated herein by reference.

In the implementation shown in FIG. 1, fermentation produces a crude ethanol mixture, which flows into a holding tank 110. Water or other solvent, and other non-ethanol components, are stripped from the crude ethanol mixture using a stripping column 112, and the ethanol is then distilled using a distillation unit 114, e.g., a rectifier. Finally, the ethanol can be dried using a molecular sieve 116, denatured if necessary, and output to a desired shipping method.

In some cases, the systems described herein, or components thereof, may be portable, so that the system can be transported (e.g., by rail, truck, or marine vessel) from one location to another. The method steps described herein can be performed at one or more locations, and in some cases one or more of the steps can be performed in transit. Such mobile processing is described in U.S. Ser. No. 12/374,549 and International Application No. WO 2008/011598, the full disclosures of which are incorporated herein by reference.

Physical Properties of the Substrate

Both functionalized substrate materials and substrate materials in their natural state can have the physical properties discussed herein.

As used herein, average fiber widths (i.e., diameters) are determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

If the substrate material is fibrous, in some cases the average length-to-diameter ratio of fibers of the substrate material can be, e.g., greater than 8/1, e.g., greater than 10/1, greater than 15/1, greater than 20/1, greater than 25/1, or greater than 50/1. An average length of the fibers can be, e.g., between about 0.5 mm and 2.5 mm, e.g., between about 0.75 mm and 1.0 mm, and an average width (i.e., diameter) of the fibers can be, e.g., between about 5 µm and 50 µm, e.g., between about 10 µm and 30 µm.

In some embodiments, a standard deviation of the length of the fibers is less than 60 percent of an average length of the fibers, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the substrate material is greater than $0.1\ m^2/g$, e.g., greater than $0.25\ m^2/g$, $0.5\ m^2/g$, $1.0\ m^2/g$, $1.5\ m^2/g$, $1.75\ m^2/g$, $5.0\ m^2/g$, $10\ m^2/g$, $25\ m^2/g$, $35\ m^2/g$, $50\ m^2/g$, $75\ m^2/g$, $100\ m^2/g$, $200\ m^2/g$, $250\ m^2/g$, $500\ m^2/g$, or even greater than $1000\ m^2/g$.

A porosity of the substrate material can be, e.g., greater than 20 percent, greater than 25 percent, greater than 35 percent, greater than 50 percent, greater than 60 percent, greater than 70 percent, e.g., greater than 80 percent, greater than 85 percent, greater than 90 percent, greater than 92 percent, greater than 94 percent, greater than 95 percent, greater than 97.5 percent, greater than 99 percent, or even greater than 99.5 percent.

Quenching and Functionalization of the Substrate

In some cases, the substrate material is functionalized by irradiation. Other techniques may also be used, as is well known in the art, for example oxidation or chemical functionalization. In some cases, functionalizing the substrate material is not part of the process, e.g., the material is used in its natural state, or is pre-functionalized by a supplier.

After treatment with ionizing radiation, the substrate material becomes ionized; that is, the material includes radicals at levels that are detectable with an electron spin resonance spectrometer. The current practical limit of detection of the radicals is about $10^{14}$ spins at room temperature. After ionization, the material can be quenched to reduce the level of radicals in the ionized material, e.g., such that the radicals are no longer detectable with the electron spin resonance spectrometer. For example, the radicals can be quenched by the application of a sufficient pressure to the material and/or by utilizing a fluid in contact with the ionized material, such as a gas or liquid, that reacts with (quenches) the radicals. The use of a gas or liquid to at least aid in the quenching of the radicals also allows the operator to control functionalization of the ionized material with a desired amount and kind of functional groups, such as carboxylic acid groups, enol groups, aldehyde groups, nitro groups, nitrile groups, amino groups, alkyl amino groups, alkyl groups, chloroalkyl groups or chlorofluoroalkyl groups. As discussed above, the functional groups imparted to the material by quenching can act as receptor sites for attachment by microorganisms or enzymes.

Detecting radicals in irradiated samples by electron spin resonance spectroscopy and radical lifetimes in such samples is discussed in Bartolotta et al., Physics in Medicine and Biology, 46 (2001), 461-471 and in Bartolotta et al., Radiation Protection Dosimetry, Vol. 84, Nos. 1-4, pp. 293-296 (1999).

In some embodiments, the quenching includes an application of pressure to the ionized material, such as by mechanically deforming the material, e.g., directly mechanically compressing the material in one, two, or three dimensions, or applying pressure to a fluid in which the material is immersed, e.g., isostatic pressing. In such instances, the deformation of the material itself brings radicals, which are often trapped in crystalline domains, in sufficient proximity so that the radicals can recombine, or react with another group. In some instances, the pressure is applied together with the application of heat, such as a sufficient quantity of heat to elevate the temperature of the material to above a melting point or softening point of the material or a component of the material. Heat can improve molecular mobility in the material, which can aid in the quenching of the radicals. When pressure is utilized to quench, the pressure can be greater than about 1000 psi, such as greater than about 1250 psi, 1450 psi, 3625 psi, 5075 psi, 7250 psi, 10000 psi or even greater than 15000 psi.

In some embodiments, quenching includes contacting the material with a fluid, such as a liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the material with a liquid, e.g., a liquid soluble in, or at least capable of penetrating into the material and reacting with the radicals, such as a diene, such as 1,5-cyclooctadiene. In some specific embodiments, the quenching includes contacting the material with an antioxidant, such as Vitamin E.

Other methods for quenching are possible. For example, any method for quenching radicals in polymeric materials described in Muratoglu et al., U.S. Patent Application Publication No. 2008/0067724 and Muratoglu et al., U.S. Pat. No. 7,166,650, can be utilized for quenching any ionized material described herein. Furthermore any quenching agent (described as a "sensitizing agent" in the above-noted Muratoglu disclosures) and/or any antioxidant described in either Muratoglu reference can be utilized to quench any ionized material.

Functionalization can be enhanced by utilizing heavy charged ions, such as any of the heavier ions described herein. For example, if it is desired to enhance oxidation, charged oxygen ions can be utilized for the irradiation. If nitrogen functional groups are desired, nitrogen ions or ions that includes nitrogen can be utilized. Likewise, if sulfur or phosphorus groups are desired, sulfur or phosphorus ions can be used in the irradiation.

After quenching, any of the quenched materials described herein can be further treated with one or more of radiation, such as ionizing or non-ionizing radiation, sonication, pyrolysis, and oxidation for additional molecular and/or supramolecular structure change.

Particle Beam Exposure in Fluids

In some cases, the substrate materials can be exposed to a particle beam in the presence of one or more additional fluids (e.g., gases and/or liquids). Exposure of a material to a particle beam in the presence of one or more additional fluids can increase the efficiency of the treatment.

In some embodiments, the material is exposed to a particle beam in the presence of a fluid such as air. Accelerated particles are coupled out of the accelerator via an output port (e.g., a thin membrane such as a metal foil), pass through a volume of space occupied by the fluid, and are then incident on the material. In addition to directly treating the material, some of the particles generate additional chemical species by interacting with fluid particles (e.g., ions and/or radicals generated from various constituents of air, such as ozone and oxides of nitrogen). These generated chemical species can also interact with the material; for example, any oxidant produced can oxidize the material.

In certain embodiments, additional fluids can be selectively introduced into the path of a particle beam before the beam is incident on the material. As discussed above, reactions between the particles of the beam and the particles of the introduced fluids can generate additional chemical species, which react with the material and can assist in functionalizing the material, and/or otherwise selectively altering certain properties of the material. The one or more additional fluids can be directed into the path of the beam from a supply tube, for example. The direction and flow rate of the fluid(s) that is/are introduced can be selected according to a desired exposure rate and/or direction to control the efficiency of the overall treatment, including effects that result from both particle-based treatment and effects that are due to the interaction of dynamically generated species from the introduced fluid with the material. In addition to air, exemplary fluids that can be introduced into the ion beam include oxygen, nitrogen, one or more noble gases, one or more halogens, and hydrogen.

Radiation Treatment

Radiation can be applied to material that is dry or wet, or even dispersed in a liquid, such as water, and can be applied while the material is exposed to air, oxygen-enriched air, or even oxygen itself, or blanketed by an inert gas such as nitrogen, argon, or helium. When maximum oxidation is desired, an oxidizing environment is utilized, such as air or oxygen.

Radiation may be applied under a pressure of greater than about 2.5 atmospheres, such as greater than 5, 10, 15, 20 or even greater than about 50 atmospheres.

In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when oxygen-containing functional groups are desired, irradiation in the presence of oxygen or even irradiation with oxygen ions can be performed. For example, when nitrogen-containing functional groups are desirable, irradiation in the presence of nitrogen or even irradiation with nitrogen ions can be performed.

Ionizing Radiation

Each form of radiation ionizes the substrate material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® system, while DC type accelerators are available from RDI, now IBA Industrial, such as the Dynamitron®.

Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused 1H-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

Gamma radiation has the advantage of a significant penetration depth into a variety of materials. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Electron Beam

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-1a-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. Typical doses may take values of 1 kGy, 5 kGy, 10 kGy, 20 kGy, 50 kGy, 100 kGy, or 200 kGy.

Ion Particle Beams

Particles heavier than electrons can be utilized to irradiate any of the substrate materials described herein. For example, protons, helium nuclei, argon ions, silicon ions, neon ions carbon ions, phoshorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam.

In some embodiments, ion beams for irradiating materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

In certain embodiments, ion beams used to irradiate materials include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$, and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4+}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

Doses

In some instances, the irradiation is performed at a dosage rate of greater than about 0.25 Mrad per second, e.g., greater than about 0.5, 0.75, 1.0, 1.5, 2.0, or even greater than about 2.5 Mrad per second. In some embodiments, the irradiating is performed at a dose rate of between 5.0 and 1500.0 kilorads/hour, e.g., between 10.0 and 750.0 kilorads/hour or between 50.0 and 350.0 kilorads/hour.

In some embodiments, the irradiating (with any radiation source or a combination of sources) is performed until the material receives a dose of at least 0.1 Mrad, at least 0.25 Mrad, e.g., at least 1.0 Mrad, at least 2.5 Mrad, at least 5.0 Mrad, at least 10.0 Mrad, at least 60 Mrad or at least 100 Mrad. In some embodiments, the irradiating is performed until the material receives a dose of from about 0.1 Mrad to about 500 Mrad, from about 0.5 Mrad to about 200 Mrad, from about 1 Mrad to about 100 Mrad, or from about 5 Mrad to about 60 Mrad. In some embodiments, a relatively low dose of radiation is applied, e.g., less than 60 Mrad.

Pyrolysis, Oxidation and Chemical Functionalization

Functionalization can also be achieved by other means, for example by pyrolysis and/or oxidation. Pyrolysis and oxidation of biomass is described at length in U.S. Ser. No. 12/417,840, the disclosure of which is incorporated by reference herein. In some cases similar methods may be used with the substrate materials described herein.

Methods of functionalizing inorganic materials are well known in the art. Examples of such methods include the techniques disclosed in "Soluble Carbon Nanotubes," Tasis et al., Chem. Eur. J. 2003, 9, 4000-4008, and "Entrapping Enzyme in a Functionalized Nanoporous Support," J. Am. Chem. Soc., 2002, 124, 11242-11243, the disclosures of which are incorporated by reference herein.

Sonication

In some cases, the material may also be sonicated, e.g., to increase porosity, e.g., using the sonication systems described in U.S. Ser. No. 12/417,840, incorporated by reference above.

Other Processes

Functionalization may be accomplished using other techniques, e.g., chemical functionalization. In some cases, Fenton chemistry may be utilized, e.g., as described in U.S. Provisional Application Ser. No. 61/147,377, the full disclosure of which is incorporated by reference herein.

Bioprocesses Utilizing the Substrate Materials

Saccharification

The substrate materials described herein can be used to enhance a saccharification reaction. In saccharification, cellulose in a feedstock, e.g., a biomass material, is hydrolyzed to low molecular carbohydrates, such as sugars, by a saccharifying agent, e.g., an enzyme. The materials that include the cellulose are treated with the enzyme, e.g., by combining the material and the enzyme in a liquid medium, e.g., in an aqueous solution.

This reaction can be enhanced by immobilizing the enzyme or other saccharifying agent on the substrate materials described herein.

Enzymes and biomass-destroying organisms that break down biomass, such as the cellulose and/or the lignin portions of the biomass, contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases). During saccharification, a cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose.

A cellulase is capable of degrading biomass and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromo-*

*sporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS117.65, *Cephalosporium* sp. RYM-202, *Acremonium* sp. CBS 478.94, *Acremonium* sp. CBS 265.95, *Acremonium persicinum* CBS169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS157.70, *Acremonium roseogriseum* CBS134.56, *Acremonium incoloratum* CBS146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei,* and *Trichoderma koningii*), alkalophilic *Bacillus* (see, for example, U.S. Pat. No. 3,844,890 and EP 458162), and *Streptomyces* (see, e.g., EP 458162) may be used.

Suitable cellobiases include a cellobiase from *Aspergillus niger* sold under the tradename NOVOZYME 188™.

Enzyme complexes may be utilized, such as those available from Genencor under the tradename ACCELLERASE®, for example, Accellerase® 1500 enzyme complex. Accellerase 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). In one embodiment, a blend of Accellerase® 1500 enzyme complex and NOVOZYME™ 188 cellobiase is used.

The saccharification process can be partially or completely performed in a tank (e.g., a tank having a volume of at least 4000, 40,000, or 400,000 L) in a manufacturing plant, and/or can be partially or completely performed in transit, e.g., in a rail car, tanker truck, or in a supertanker or the hold of a ship. The time required for complete saccharification will depend on the process conditions and the feedstock and enzyme used. If saccharification is performed in a manufacturing plant under controlled conditions, the cellulose may be substantially entirely converted to glucose in about 12-96 hours. If saccharification is performed partially or completely in transit, saccharification may take longer. The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the resulting glucose solution be relatively high, e.g., greater than 40%, or greater than 50, 60, 70, 80, 90 or even greater than 95% by weight. This reduces the volume to be shipped, and also inhibits microbial growth in the solution. However, lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high.

A relatively high concentration solution can be obtained by limiting the amount of water added to the feedstock with the enzyme. The concentration can be controlled, e.g., by controlling how much saccharification takes place. For example, concentration can be increased by adding more feedstock to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

Fermentation

Microorganisms can produce a number of useful intermediates and products, such as those described herein, by fermenting a low molecular weight sugar in the presence of the functionalized substrate materials. For example, fermentation or other bioprocesses can produce alcohols, organic acids, hydrocarbons, hydrogen, proteins or mixtures of any of these materials.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Sacchromyces* spp. e.g., *Sacchromyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae, Pichia stipitis* (a relative of *Candida shehatae*, the genus *Clavispora*, e.g., species *Clavispora lusitaniae* and *Clavispora opuntiae* the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeasts include, for example, Red Star®/Lesaffre Ethanol Red (available from Red Star/Lesaffre, USA) FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Bacteria may also be used in fermentation, e.g., *Zymomonas mobilis* and *Clostridium thermocellum* (Philippidis, 1996, supra).

The optimum pH for yeast is from about pH 4 to 5, while the optimum pH for *Zymomonas* bacteria is from about pH 5 to 6. Typical fermentation times are about 24 to 96 hours with temperatures in the range of 26° C. to 40° C., however thermophilic microorganisms prefer higher temperatures.

In some embodiments, all or a portion of the fermentation process can be interrupted before the low molecular weight sugar is completely converted to ethanol. The intermediate fermentation products include high concentrations of sugar and carbohydrates. These intermediate fermentation products can be used in preparation of food for human or animal consumption. Additionally or alternatively, the intermediate fermentation products can be ground to a fine particle size in a stainless-steel laboratory mill to produce a flour-like substance.

Mobile fermentors can be utilized, as described in U.S. Provisional Patent Application Ser. 60/832,735, now Published International Application No. WO 2008/011598.

Post-Processing

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Intermediates and Products

The processes described herein can be used to produce one or more intermediates or products, such as energy, fuels, foods and materials. Specific examples of products include, but are not limited to, hydrogen, alcohols (e.g., monohydric alcohols or dihydric alcohols, such as ethanol, n-propanol or n-butanol), hydrated or hydrous alcohols, e.g., containing greater than 10%, 20%, 30% or even greater than 40% water, xylitol, sugars, biodiesel, organic acids (e.g., acetic acid and/or lactic acid), hydrocarbons, co-products (e.g., proteins, such as cellulolytic proteins (enzymes) or single cell proteins), and mixtures of any of these in any combination or relative concentration, and optionally in combination with any additives, e.g., fuel additives. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha, beta unsaturated acids, such as acrylic acid and olefins, such as ethylene. Other alcohols and alcohol derivatives include propanol, propylene glycol, 1,4-butanediol, 1,3-propanediol, methyl or ethyl esters of any of these alcohols. Other products include methyl acrylate, methylmethacrylate, lactic acid, propionic acid, butyric acid, succinic acid, 3-hydroxypropionic acid, a salt of any of the acids and a mixture of any of the acids and respective salts.

Other intermediates and products, including food and pharmaceutical products, are described in U.S. Ser. No. 12/417,900, the full disclosure of which is hereby incorporated by reference herein.

Other Embodiments

A number of embodiments of the invention have been described. Nevertheless, it will be understood that various modifications may be made without departing from the spirit and scope of the invention.

For example, the fibers can be in any desired form, and can have a variety of different morphologies. Generally, it is desirable that the fibrous material have a high surface area. In some cases, the fibers may be incorporated into single or multi-layer sheets, e.g., the fibers may be part of a HEPA filter or the like. The sheet material can have a surface area of, for example, from about 1 to 500 $m^2/g$. The fibrous material can be overlaid, e.g., meltblown, folded, in the form of a screen or mesh, or provided in other geometries. The fibers may be extruded or coextruded.

The fibers may have any desired particle size, from nanoscale, e.g., less than about 1000 nm, e.g., less than 500 nm, 250 nm, 100 nm, 50 nm, 25 nm, or even less than 1 nm, to large particle sizes, e.g., greater than 100 microns, 200 microns, 500 microns or even 1000 microns, or agglomerates of particles.

The fibers or a fibrous material containing the fibers may be pretreated with a microorganism and/or enzyme, and/or the fibers or fibrous material can be contacted with a microoganism and/or enzyme during a bioprocess such as saccharification or fermentation.

While inorganic and synthetic substrate materials have been discussed herein, these materials may be combined with other substrate materials, for example the biomass substrates disclosed in U.S. Provisional Application No. 61/252,293, filed Oct. 16, 2009, the full disclosure of which is incorporated herein by reference.

As discussed above, enzymes can be immobilized on the fibers, instead of or in addition to microorganisms.

Accordingly, other embodiments are within the scope of the following claims.

What is claimed is:

1. A mixture comprising:
    an inorganic material in the form of particles or fibers and said inorganic material having polar functional groups,
    a microorganism or enzyme each having complementary functional groups and having an attractive interaction to the functional groups of the inorganic material,
    a saccharified material, and
    a solvent, wherein
    the inorganic material has been functionalized by irradiating the material with ionizing radiation and subsequently quenching the irradiated material with a quenching agent suitable for producing the polar functional groups, and
    wherein the inorganic material is selected from the group consisting of calcium carbonate, aragonite clay, orthorhombic clays, calcite clay, rhombohedral clays, kaolin, bentonite clay, dicalcium phosphate, tricalcium phosphate, calcium pyrophosphate, insoluble sodium metaphosphate, magnesium orthophosphate, trimagnesium phosphate, hydroxyapatites, synthetic apatites, alumina, hydrated alumina, silica xerogel, metal aluminosilicate complexes, sodium aluminum silicates, zirconium silicate, silicon dioxide, graphite, wollastonite, mica, glass, fiber glass, silica, talc, carbon fibers, conductive carbon black, ceramic powders and ceramic fibers, alumina trihydrate, ground construction waste, and mixtures thereof.

2. The mixture as in claim 1, wherein the microorganism or enzyme is attached to the inorganic material by the attractive interaction between the complementary functional group on the microorganism or enzyme and the polar functional groups on the inorganic material.

3. The mixture as in claim 1 wherein the inorganic material is a synthetic material.

4. The mixture as in claims 1 wherein the polar functional groups on the inorganic material are carboxylate groups.

5. The mixture as in claim, 1 wherein the polar functional groups on the inorganic material is selected from the group consisting of aldehyde groups, nitroso groups, nitrile groups, nitro groups, ketone groups, amino groups, alkyl amino groups, alkyl groups, chloroalkyl groups, chlorofluoroalkyl groups, and enol groups.

6. The mixture as in claim 1, wherein the microorganism is yeast.

7. The mixture as in claim 1, wherein the microorganism is a bacterium.

8. The mixture as in claim 1 wherein the enzyme is a cellulase.

9. The mixture as in claim 1, wherein the particles or fibers have a Brunauer Emmett Teller (BET) surface area of greater than 100 $m^2/g$.

10. The mixture as in claim 1 wherein the particles or fibers have a porosity of greater than 70%.

11. The mixture as in claim 1 wherein the particles or fibers have a porosity of greater than 90%.

12. The mixture as in claim 1 wherein the particles or fibers are provided in the form of a single or multi-layer sheet.

13. The mixture as in claim 1 wherein the particles or fibers are provide in the form of a fibrous material that is overlaid, folded, or in the form of a screen or mesh.

14. The mixture as in claim 1 wherein the fibers or particles are extruded or coextruded.

15. The mixture as in claim 1 wherein the fibers or particles have a nano-scale average particle size.

16. The mixture as in claim 1, wherein the saccharified material comprises a sugar selected from the group consisting of sucrose, glucose, xylose, or a mixture thereof.

17. The mixture as in claim 1 further comprising ethanol.

* * * * *